(12) United States Patent
Choi et al.

(10) Patent No.: US 11,129,706 B2
(45) Date of Patent: Sep. 28, 2021

(54) PROSTHESIS FOR IN VIVO INSERTION, COATED WITH CROSS-LINKED POLYPHOSPHORYLCHOLINE

(71) Applicants: SEOUL NATIONAL UNIVERSITY R&DB FOUNDATION, Seoul (KR); BS RESEARCH CO. LTD., Seoul (KR)

(72) Inventors: Tae Hyun Choi, Seoul (KR); Yan Lee, Seoul (KR); Ji Ung Park, Seoul (KR); Ji Yeon Ham, Changwon-si (KR); Hee Jin Kim, Pyeongtaek-si (KR); Suk Wha Kim, Seoul (KR); Hye Jeong Min, Seoul (KR)

(73) Assignees: SEOUL NATIONAL UNIVERSITY R&DB FOUNDATION, Seoul (KR); BS RESEARCH CO. LTD., Seoul (KR)

( * ) Notice: Subject to any disclaimer, the term of this patent is extended or adjusted under 35 U.S.C. 154(b) by 225 days.

(21) Appl. No.: 15/304,780

(22) PCT Filed: Apr. 17, 2015

(86) PCT No.: PCT/KR2015/003879
§ 371 (c)(1),
(2) Date: Oct. 17, 2016

(87) PCT Pub. No.: WO2015/160218
PCT Pub. Date: Oct. 22, 2015

(65) Prior Publication Data
US 2017/0035555 A1 Feb. 9, 2017

(30) Foreign Application Priority Data
Apr. 17, 2014 (KR) .................. 10-2014-0045713

(51) Int. Cl.
*C08F 2/12* (2006.01)
*A61F 2/12* (2006.01)
(Continued)

(52) U.S. Cl.
CPC .............. *A61F 2/12* (2013.01); *A61F 2/0059* (2013.01); *A61F 2/0063* (2013.01); *A61L 27/28* (2013.01);
(Continued)

(58) Field of Classification Search
CPC ........ A61F 2/12; A61F 2/0059; A61F 2/0063; C08F 2/48; A61L 27/32; A61L 27/28; A61L 27/34
See application file for complete search history.

(56) References Cited

U.S. PATENT DOCUMENTS

2004/0185081 A1* 9/2004 Verlee ................. A61F 2/91
424/423
2005/0015046 A1* 1/2005 Weber ............... A61M 25/1029
604/96.01
(Continued)

FOREIGN PATENT DOCUMENTS

CN 102091355 A * 6/2011
CN 10-3130958 A 6/2013
(Continued)

OTHER PUBLICATIONS

Goda et al., "Biomimetic phosphorylcholine polymer grafting from polydimethylsiloxane surface using photo-induced polymerization," *Biomaterials* 27:5151-5160 (2006).
(Continued)

*Primary Examiner* — Ling Siu Choi
*Assistant Examiner* — David L Miller
(74) *Attorney, Agent, or Firm* — Seed Intellectual Property Law Group LLP (57) ABSTRACT

The present invention relates to a coating composition for an in-vivo implantable prosthesis including a photoinitiator, a
(Continued)

Normal coating method (Normal)

New coating method using crosslinking (Crosslinked)

crosslinking agent, and a phosphorylcholine (PC) monomer having an acrylate group, a method of coating an in-vivo implantable prosthesis using the coating composition, and a cosmetic prosthesis coated with the crosslinked polyphosphorylcholine.

An in-vivo implantable prosthesis coated with crosslinked polyphosphoryicholine may be manufactured by a simple method of applying a coating composition including a photoinitiator, a crosslinking agent, and a phosphorylcholine (PC) monomer having an acrylate group according to the present invention, and then irradiating UV rays. The crosslinked polyphosphorylcholine coating may provide hydrophilicity for the surface and may also remarkably reduce adsorption of proteins and fibroblasts, which may cause side effects such as capsular contracture. Further, the coating has strong enough not to peel off even under stimulation, and therefore, it is maintained under vigorous activity after implantation, thereby being usefully applied to the manufacture of an in-vivo implantable prosthesis with reduced side effects, such as breast prosthesis for cosmetic surgery.

8 Claims, 8 Drawing Sheets (51) Int. Cl.
*A61L 27/32* (2006.01)
*A61L 27/34* (2006.01)
*A61L 27/28* (2006.01)
*A61F 2/00* (2006.01)
*B05D 1/02* (2006.01)
*C08F 2/48* (2006.01)

(52) U.S. Cl.
CPC ............... *A61L 27/32* (2013.01); *A61L 27/34* (2013.01); *B05D 1/02* (2013.01); *A61F 2002/009* (2013.01); *A61F 2002/0086* (2013.01); *A61L 2300/216* (2013.01); *A61L 2400/18* (2013.01); *A61L 2430/04* (2013.01); *C08F 2/48* (2013.01)

(56) References Cited

U.S. PATENT DOCUMENTS

| 2005/0266038 | A1  | 12/2005 | Glauser et al. |
| 2007/0254005 | A1* | 11/2007 | Pathak ................... A61K 35/12 424/423 |
| 2011/0274940 | A1  | 11/2011 | Kyomoto et al. |
| 2014/0248475 | A1  | 9/2014  | Kasai |
| 2014/0322468 | A1* | 10/2014 | Minagawa ............. C08G 69/48 428/36.8 |

FOREIGN PATENT DOCUMENTS

| JP | 2013-070796 A | 4/2013 |
| KR | 10-2006-0015624 A | 2/2006 |
| WO | WO-9305081 A1 * | 3/1993 ......... A61L 33/0088 |
| WO | 03/030940 A1 | 4/2003 |
| WO | 2011/086537 A2 | 7/2011 |

OTHER PUBLICATIONS

Kobayashi et al., "Segmented polyurethane modified by photopolymerization and cross-linking with 2-methacryloyloxyethyl phosphorylcholine polymer for blood-contacting surfaces of ventricular assist devices," *J Artif Organs* 8:237-244 (2005).

Zeplin et al., "Phosphorylcholine-Coated Silicone Implants," *Annals of Plastic Surgery* 65(6):560-564 (Dec. 2010).

Huang et al., "Surface modification of silicone intraocular lens by 2-methacryloyloxyethyl phosphoryl-choline binding to reduce *Staphylococcus epidermidis* adherence," *Clinical and Experimental Opththalmology* 35:462-467 (2007).

* cited by examiner

[FIG. 1]

Normal coating method (Normal)

New coating method using crosslinking (Crosslinked)

In vivo comparison of capsules formed in rate

PROSTHESIS FOR IN VIVO INSERTION, COATED WITH CROSS-LINKED POLYPHOSPHORYLCHOLINE

BACKGROUND OF THE INVENTION

1. Field of the Invention

The present invention relates to a coating composition for an in-vivo implantable prosthesis including a photoinitiator, a crosslinking agent, and a phosphorylcholine (PC) monomer having an acrylate group, a method, of coating the in-vivo implantable prosthesis using the coating composition, and a cosmetic prosthesis coated with the crosslinked, polyphosphorylcholine.

2. Description of the Related Art

With development of the medical technology, tissue or organ transplantation was realized. However, due to a lack of amount of human tissue or organ supply, artificial tissue or organ has been developed as a substitute, alternatively. To provide in-vivo implantable artificial tissues or organs, diverse biomaterials have been developed and applied. These biomaterials are required to have physical properties (strength, viscosity, elasticity, etc.) similar to those of actual tissues or organs, and their prices should be also stabilized so that many patients can use them. Although many efforts have been made to explore these biomaterials, applicable biocompatible materials are still limited, and many of commercially available materials often induce side effects. One of representative side effects is capsular contracture which occurs after in vivo implantation of a cosmetic prosthesis used in breast augmentation/reconstruction. Breast augmentation procedure accounts for about 20% of the world's cosmetic surgery procedures, and when a reconstruction surgery following mastectomy of breast cancer patients is included, the percentage further increases. The surface of the most popularly used cosmetic breast implants is made of a material called polydimethylsiloxane (PDMS), and has chemical properties different from those of the actual breast tissue, and therefore, about 17.5% of the patients who received the breast augmentation/reconstruction surgery experience a side-effect of capsular contracture in which abnormal fibrous tissues surround the breast implant. Capsular contracture causes severe pain for patients. Further, in severe cases, capsular contracture should be managed with surgical capsulectomy, leading to psychological/economic loss of patients. Therefore, many methods have been developed to prevent capsular contracture, but successful outcomes were reported in rare cases. Such, side effect is the most frequent complication that may be generated after other most prosthetic surgeries as well as mammoplasty. As described above, there is no special therapy for the side-effect, except for surgical removal. Even though surgical removal is performed, complete removal is also not easy in the case of severe cellular adsorption of tissues to the prosthetic implant. Therefore, surgical removal may be accompanied by serious after-effects to reduce the patient's quality of life and to increase medical expenses due to increased costs of treatment and management, leading to socioeconomic loss.

As described above, once a prosthetic implant is implanted in the body, a capsule is formed by a body's defense mechanism to isolate the foreign body from the tissue, and excessive capsular formation with collagen-fiber capsule thickening causes pain and deformity of the prosthetic implant. Many artificial prostheses implanted from the outside are recognized as foreign materials in the body, and a variety of proteins in the body fluid are adsorbed thereto. Subsequent biochemical processes occur to cause thrombus formation, immune response, tissue deformation, necrosis and/or degeneration. Therefore, for accomplishment of biocompatible prosthetic implants including reduction of capsular contracture, the most important factor is to prevent recognition of the prosthesis as a foreign material by coating the surface with a biocompatible material. At present, to reduce capsular contracture caused by excessive foreign body reactions of cosmetic prosthesis, there have been many attempts of changing the site of implantation, washing of the implant with an antibiotic, using steroid, fabricating the surface of the implant as a textured type, etc. However, there has been no method, of preventing the fundamental mechanism whereby the prosthetic implant is recognized as a foreign body.

Polydimethylsiloxane (PDMS)-based materials used as representative surface materials for in-vivo implantable prostheses have been applied to various medical devices, such as ophthalmic biomaterials, microfluidic devices, artificial lung and artificial finger joint, due to high oxygen permeability, excellent mechanical property, optical transparency, self-sealing property, convenient processability and chemical stability. Meanwhile, intrinsic hydrophobicity and bioadhesion of PDMS are significant obstacles for its use as biomaterials. For example, it is accepted that non-specific protein adsorption to the material is recognized as the first stage in incurring subsequent events including thrombus formation, foreign body reaction, bacterial infection, and other undesired reactions. In an ultrasensitive analysis of a microfluidic system, adsorption of biomolecules onto PDMS remarkably reduces a signal-to-noise ratio during detection. An important issue in artificial lungs is blood, activation in a large blood-contacted area. Therefore, a method of modifying the surface property of PDMS in a rapid and easy way is required.

Current polymer coating technologies themselves are rapidly developed, but their applications to bioimplants are extremely rare. There is a report of application of polymer coating on metallic surface of stents for drug eluting stents, etc., but the coating method still remains only at the level of spray coating. Recently, biomimetic synthetic phospholipid polymers are studied in various fields. In particular, PMPC (poly(methacryloyloxyethyl polyphosphorylcholine)) which is a polymer of MFC (2-methacryloyloxyethyl polyphosphorylcholine) has a structure similar to the head group of phosphatidylcholine which is one of phospholipids constituting the cell membrane of human body, and therefore, PMPC exhibits biocompatibility, hemocompatibility including antithrombotic activity, and anti-adsorption or anti-adhesion activity against proteins or cells, thereby being applied to drug delivery and tissue engineering and being used as a surface material for diverse biomaterials. Accordingly, PMPC (polymethaacryloyloxyethyl polyphosphorylcholine) has been already used as a coating material for bioimplants such as drug eluting stents, and showed excellent biocompatibility.

The present inventors have made intensive studies to manufacture a silicone prosthesis, in which foreign body reactions caused by artificial prosthetic bioimplants are suppressed, by using cell membrane-mimic polymers. As a result, they found that when the surface of silicone prosthesis is coated with a polymer that mimics phosphatidylcholine (PC) as a major constituent, of cell membrane phospholipids while crosslinking the phosphatidylcholine polymer chains to each other by further adding a crosslinking agent, the silicone prosthesis exhibits biocompatibility upon being implanted in the body to suppress foreign body reactions, and also exhibits improved coating strength due to the crosslinking to prevent the coating from peeling off even under strong mechanical stimulation, thereby completing the present invention.

SUMMARY OF THE INVENTION

An object of the present invention is to provide a coating composition for an in-vivo implantable prosthesis, including a photoinitiator, a crosslinking agent, and a phosphorylcholine (PC) monomer having an acrylate group.

Another object of the present invention is to provide a method of coating an in-vivo implantable prosthesis, the method including the steps of applying the coating composition to the in-vivo implantable prosthesis; and irradiating UV rays onto the in-vivo implantable prosthesis to which the coating composition is applied.

Still another object of the present invention is to provide an in-vivo implantable prosthesis coated with the crosslinked polyphosphorylcholine.

DETAILED DESCRIPTION OF THE PREFERRED EMBODIMENTS

In an aspect to achieve the above objects, the present invention provides a coating composition for an in-vivo implantable prosthesis, including a photoinitiator, a crosslinking agent, and a phosphorylcholine (PC) monomer having an acrylate group.

The present invention is characterized in that, based on the idea that a polymerization reaction of phosphorylcholine monomer having an acrylate group by radicals generated from a known photoinitiator upon UV irradiation forms a linear phosphorylcholine polymer, a crosslinking agent is further added to form a crosslinked network-type polymer membrane instead of the linear phosphorylcholine polymer. The network-type polymer membrane crosslinked by the crosslinking agent has improved coating strength, and therefore, it is not damaged by strong mechanical stimulation such as sonication. There is a report that a prosthesis coated with the linear phosphorylcholine polymer also exhibits reduced protein and/or cell adherence, thereby reducing capsular contracture which may occur in patients after breast augmentation surgery. However, the prosthesis continuously undergoes body movement and/or physical stimulus (pressure or distortion) in the body over time, and therefore, the coating may peel off. In this case, the reduced side-effects of the coated prosthesis are not ensured. Accordingly, there is a demand for a coating which is strong enough not to be damaged by rather strong stimulation. In order to solve this problem, therefore, the present invention is characterized in that a composition further including a crosslinking agent is used, to form a network-type polymer, and an in-vivo implantable prosthesis is coated, with this network-type polymer, thereby providing a coating with improved, strength, compared to a known linear polymer.

As used herein, the term "in-vivo implantable prosthesis", also simply "prosthesis", refers to a structure that is implanted into the body for reconstruction or replacement of damaged or defective tissue, for cosmetic surgery, or for therapy, and for example, it may be a solid-type structure or a sealed sac-type structure with fluidity.

The in-vivo implantable prosthesis which may be coated with the coating composition of the present invention may be a material, having a functional group which, may provide radicals capable of binding with a terminal C=C bond of acrylate by a photoinitiator so that the phosphorylcholine monomer having the acrylate group as a component of the coating composition forms a covalent bond with the external surface of the prosthesis via the terminal C=C bond of the acrylate group. Any materials used in the in-vivo implantable prosthesis known in the art, excluding metals or hydrophilic ethylene-based materials, may be used without limitation. For example, the external surface of the in-vivo implantable prosthesis may include polydimethylsiloxane (PDMS)-based, hydroxyapatite (HA), polylactic acid (PLA)-based, polyglycolic acid (PGA)-based, polytetrafluoroethylene (PTFE)-based, polyethylene terephthalate (PET)-based, polypropylene-based, polyamide-based, polyacetal-based, polyester-based, or polymethyl methacrylate-based materials, but is not limited thereto.

Preferably, the phosphorylcholine monomer having the acrylate group may be methacryloyloxyethylphosphorylcholine (MPC) or acryloyloxyethylphosphorylcholine (APC), but is not limited thereto. It is not limited to a specific chemical formula, and may include an acrylate-based monomer including methacrylate containing phosphorylcholine or zwitterion containing phosphorus and nitrogen regardless of the linkage type without limitation.

As used herein, the term "photoinitiator" refers to a substance capable of generating radicals upon receiving light. Therefore, radicals are generated by irradiation of light to the photoinitiator, thereby inducing radical polymerization. In this regard, the light may be preferably UV. The radical polymerization reaction may be a polymerization method of forming a polymer by successive addition of free radicals, in which the radicals may be commonly formed via a number of different mechanisms usually involving separate initiator molecules.

Once the reaction is initiated, the formed radical uses one electron from the pi bond of a polymer monomer containing a double bond to form a stable single bond. The double bond is converted to a single bond, and a new radical containing the other electron is generated in the other carbon atom of the monomer that does not form the single bond with the previous radical. The above described, process is repeated via the newly formed radical, and as a result, a polymer chain growth continues.

Preferably, the photoinitiator may be benzophenone, benzoyl peroxide, azobisisobutyronitrile (AIBN), or 2,2-dimethoxy-2-phenylacetophenone (DMPA), but is not limited thereto.

Preferably, the crosslinking agent may be selected from the group consisting of dipentaerythritol pentaacrylate, dipentaerythritol hexaacrylate, ethyleneglycol diacrylate, ethyleneglycol dimethacrylate, allyl methacrylate, acetoacetoxyethyl methacrylate, isocyanatoethyl methacrylate, isobutyl methacrylate, normal-butyl methacrylate, and combinations thereof, but is not limited thereto.

Preferably, the coating composition according to the present invention may include the photoinitiator in an amount of 0.01 to 0.2 mol. % with respect to the phosphorylcholine monomer, but is not limited thereto.

Preferably, the coating composition according to the present invention may include the crosslinking agent in an amount of 0.01 to 2.0 mol % with respect to the phosphorylcholine monomer, but is not limited thereto.

If the amount(s) of the photoinitiator and/or crosslinking agent used is(are) lower than the lowest limit of the above range, that is, lower than 0.01 mol %, the amount of the polymer produced on the surface, for example, the number of the polymer strand and/or the length (molecular weight) of each polymer strand, is(are) remarkably reduced, and thus MPC does not cover the surface of the prosthesis evenly and sufficiently, or sufficient crosslinking does not occur. Consequently, desired, physical properties are not obtained or desired coating strength is not obtained, and the coating may peel off during a washing process. In contrast, if the amount (s) of the photoinitiator and/or crosslinking agent used is(are) higher than the upper limit of the above range, that is, the content of the photoinitiator exceeds 0.2 mol % or the content of the crosslinking agent exceeds 2.0 mol %, excess crosslinking occurs, and therefore, the prosthesis may not have desired elasticity and may be excessively hardened to cause an unnecessary waste of the sample.

In another aspect, the present invention provides a method of coating the in-vivo implantable prosthesis, the method including the steps of applying the coating composition according to the present invention to the in-vivo implantable prosthesis; and irradiating UV rays onto the in-vivo implantable prosthesis to which the coating composition is applied.

Preferably, for uniform coating of the surface of the in-vivo implantable prosthesis, the coating composition may be applied to be evenly contacted with, the surface of the prosthesis, followed by UV irradiation.

In another aspect, the present invention provides an in-vivo implantable prosthesis coated with the crosslinked polyphosphorylcholine.

Definition and features of the in-vivo implantable prosthesis are the same as described above.

Preferably, the in-vivo implantable prosthesis may be manufactured by applying the coating composition according to the present invention to the surface of the prosthesis, and then performing crosslinking reaction, but is not limited thereto. The crosslinking reaction may be performed by using a method known in the art without limitation. For example, the crosslinking reaction may be performed by UV irradiation.

Preferably, the in-vivo implantable prosthesis may be used for reconstruction or replacement of damaged or defective tissue, for cosmetic surgery, or for therapy, and for example, breast augmentation/reconstruction, but is not limited thereto.

For example, the breast prosthesis for cosmetic surgery which is coated, with the crosslinked polyphosphorylcholine according to the present invention exhibits remarkably reduced adsorption of protein and fibroblast, thereby reducing induction of side effects such as capsular contracture, and it also has enhanced coating strength not to peel off even, under strong mechanical activity of stimulation, and therefore, maintains stable after vigorous activity. Accordingly, there is no concern about deterioration of the function by peeling of the coating over time.

Hereinafter, the present invention will be described in more detail with reference to Examples. However, these Examples are for illustrative purposes only, and the scope of the present invention is not intended to be limited by these Examples.

Example 1: Preparation of Crosslinked PMPC-Coated PDMS

An initiation solution containing 10 g/L of benzophenone as a photoinitiator and dipentaerythritol penta(or hexa)acrylate as a crosslinking agent and a monomer solution containing 0.50 M methacryloyloxyethyl phosphorylcholine (MPC) as a monomer of a polymer and ethylene glycol dimethacrylate (EGDMA) as a crosslinking agent were applied to a prosthesis made of a silicone (polydimethysiloxane, polydimethylsiloxane; PDMS) material, and the prosthesis was irradiated with UV for 15 minutes at a distance of 15 cm to be coated by radical polymerization reaction. All photoinitiator solutions were prepared by using acetone as a solvent irrespective of the type and presence of the crosslinking agent. All MPC solutions were prepared by using deionized water as a solvent irrespective of the type and presence of the crosslinking agent. If necessary, oxygen was removed, from the monomer solution. The composition of the solution is given in the following Table together with a composition of a solution which was used in a non-crosslinking coating method as a control group. In detail, the crosslinking agents, dipentaerythritol penta(or hexa)acrylate and ethylene glycol dimethacrylate were used in an amount of 0.5 mol % and 1 mol % with respect to the used monomer MPC, respectively. The coated prosthesis was washed by sonication for 10 minutes twice to remove residual reactants before use in analysis. The washing method by sonication is a rather extreme method, compared to a washing method commonly used. This rather strong washing method was used to mimic movement after in vivo implantation, which may cause peeling off of the coating.

Comparative Example 1: Preparation of PMPC-coated PDMS

In order to examine the effect of the crosslinked PMPC coating prepared by using the initiation solution according to the present invention, a silicone prosthesis was coated in the same manner as in Example 1, except that no crosslinking agents were included in the initiation solution and the monomer solution. The composition of each solution is given in the following Table 1. The conditions for radical reaction and the washing method are also given in Table 1.

contact angle. The obtained images and water contact angles determined therefrom are shown in FIG. 2.

Figure 1:
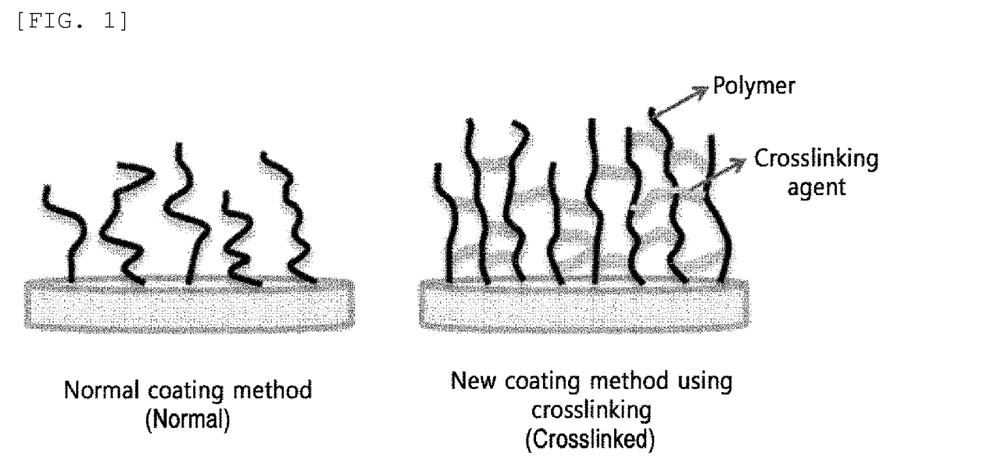
FIG. 1 is a schematic illustration showing a coating method, using cross linking (Crosslinked according to the present invention and a normal coating method (Normal)
Figure 2:
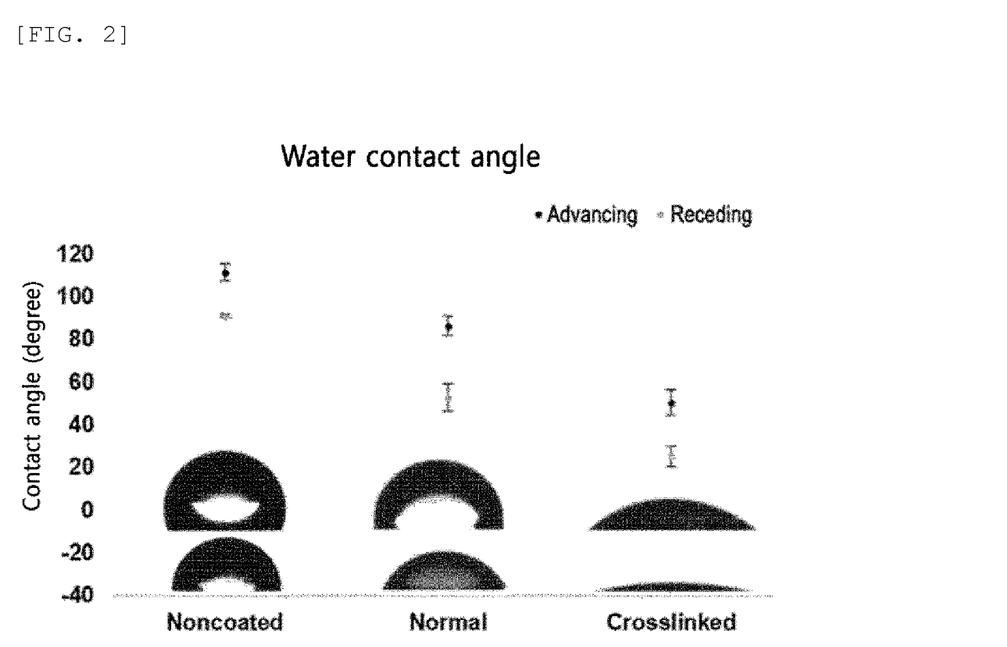
FIG. 2 shows water contact angles of a surface prepared by the coating method using cross linking according to the present invention, a surface prepared by the normal coating method, and a non-coated, surface.

As shown in FIG. 2, since the non-coated PDMS used as the negative control possessed high hydrophobicity, it showed high water contact angles in both the advancing contact angle and the receding contact angle, but the values were remarkably decreased on the surface coated with PMPC, and the values were further decreased on the surface coated with crosslinked PMPC. That is, it was confirmed that the surface becomes hydrophilic by PMPC coating and more hydrophilic by crosslinking thereof.

TABLE 1

| | | Normal coating method | New coating method using crosslinking |
|---|---|---|---|
| Composition of initiation solution | Initiator: benzophenone | 10 g/L | 10 g/L |
| | Crosslinking agent: dipentaerythritol penta-/hexa-acrylate (structure shown; R = H or acryloyl) | n/a | 0.50 mol % to MPC |
| Composition of monomer solution constituting polymer | Monomer: MPC | 0.50 M | 0.50 M |
| | Crosslinking agent: ethyleneglycol dimethacrylate (structure shown) | n/a | 1 mol % to MPC |
| | UV irradiation time | | 15 min |
| | UV irradiation distance | | 15 cm |
| | Washing conditions before analysis | | Sonication 10 min × 2 |

Experimental Example 1: Measurement of Water Contact Angle

The change of hydrophilicity of the surface of PDMS prosthesis which was coated with crosslinked or non-crosslinked PMPC prepared in Example 1 (Crosslinked) and Comparative Example 1 (Normal) was examined by measuring water contact angle. As a negative control, non-coated PDMS (Noncoated) was used. In detail, of dynamic water contact angle measurements, a captive drop method was used, to measure an advancing contact angle and a receding contact angle. The advancing contact angle was obtained by measuring an angle between the surface and a water drop when the volume of deionized water on the surface was increased from 0 μl to 6 μl using a needle, and the receding contact angle was obtained by measuring an angle between the surface and a water drop when the volume of deionized water on the surface was decreased from 6 μl to 3 μl using a needle. The advancing contact angle is a value that represents hydrophobicity of the surface and the receding contact angle is a value that represents hydrophilicity of the surface. In the present invention, the change of the receding contact angle was greater than that of the advancing contact angle, and thus, information about hydrophilicity of the surface was obtained from the change of the receding

Experimental Example 2: Surface Elemental Analysis by XPS

In order to examine whether the change of the water contact angle, namely, the change of hydrophilicity confirmed in Experimental Example 1 is attributed to introduction of the phosphorylcholine group, surface elemental analysis was performed using XPS. The results are shown in FIG. 3.

Figure 3:
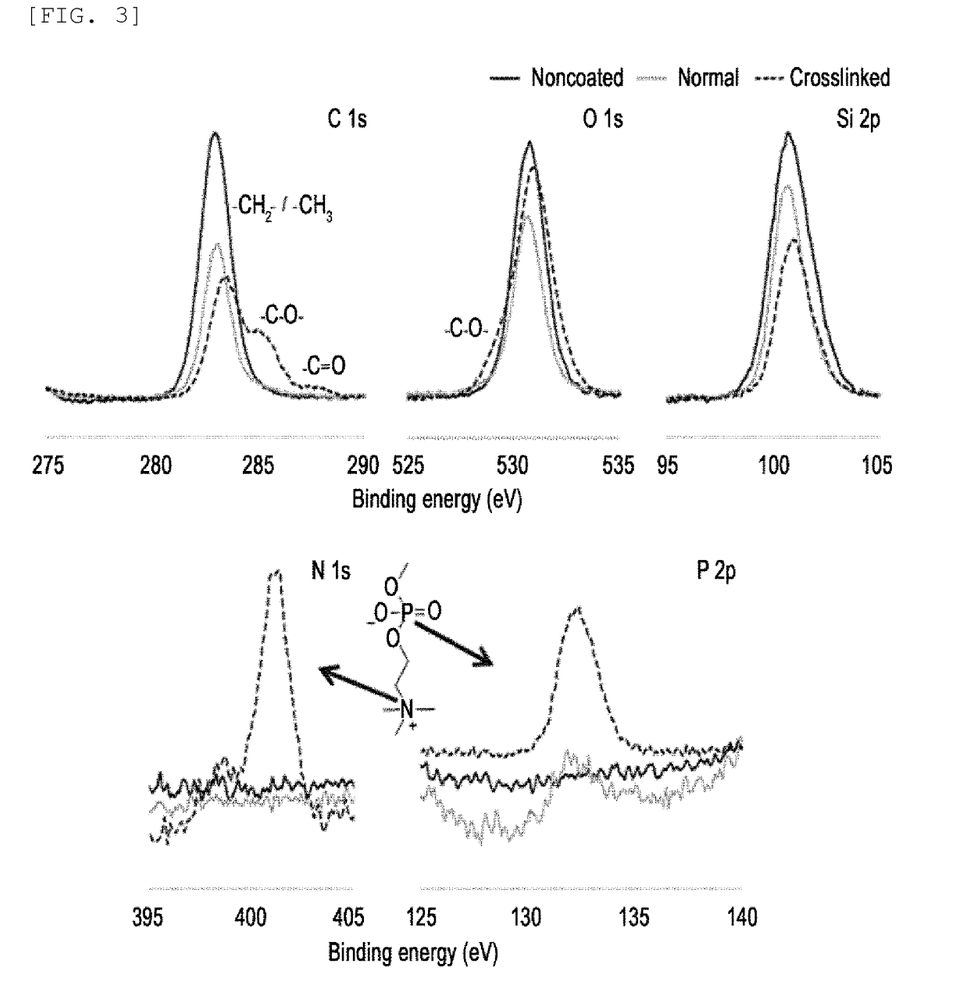
FIG. 3 shows the results of surface elemental analysis by XPS for the surface prepared by the coating method using crosslinking according to the present invention, the surface prepared by the normal coating method, and the non-coated surface.

As shown in FIG. 3, the surface coated, with cross linked PMPC maintained, the similar oxygen content, but a remarkably reduced carbon and/or silicon ratio, compared to the non-coated PDMS. In detail, with regard to the carbon peaks, the peaks of methylene and/or methyl were greatly decreased, but the peaks of —C—O— and —C=O bonds was observed by the crosslinked PMPC coating. Further, the contents of nitrogen and phosphorus which were not detected in the non-coated PDMS were greatly increased in the crosslinked PMPC-coated surface. When these results are compared to the results of measuring the water contact angle which was remarkably reduced on the surface coated with crosslinked PMPC, the reduction in the water contact angle, namely, the increase in the hydrophilicity was consistent with an increase in the contents of oxygen, nitrogen, and/or phosphorus with relatively high electronegativity on the surface, also indicating an increase in the content of the phosphorylcholine group containing these elements.

Meanwhile, the surface coated with non-crosslinked PMPC showed no apparent nitrogen and/or phosphorous peaks. It may be because the coating was considerably damaged by strong-washing using sonication or the effect of increasing the amount of the polymer coated on the surface by the crosslinking agent was not considered, indicating that the coating of the crosslinked PMPC according to the present invention is not damaged, under strong mechanical stimulation due to crosslinking.

Experimental Example 3: Measurement of Protein Adsorption

The protein adsorption onto the surface of PDMS prosthesis which was coated, with crosslinked or non-crosslinked PMPC prepared in Example 1 (Crosslinked) and Comparative Example 1 (Normal) was examined by BCA assay. As a negative control, non-coated PDMS (Noncoated) was used. As the protein, BSA (bovine serum albumin) and BPF (bovine plasma fibrinogen) were used. Non-coated PDMS, PMPC-coated PDMS, and crosslinked PMPC-coated PDMS were incubated with BSA at a concentration of 4.5 mg/ml or BPF at a concentration of 0.3 mg/ml at 37° C. for 1 hour, respectively. Under respective conditions, PDMS was washed gently with fresh DPBS buffer at 37° C. and 200 rpm for 1 minute twice. Next, to quantify the protein adsorbed onto the surface, BCA assay was performed. In detail, a BCA kit of Thermo Scientific Co., Ltd. was used. Sample A, Sample B and Sample C included in the kit were mixed, at a volume ratio of 25:24:1 to prepare an assay solution. Each of the washed PDMS was immersed in fresh DPBS buffer, and an equal volume of the assay solution was added thereto, followed by incubation at 60° C. for 1 hour. Absorbance at 570 nm was measured to determine the relative quantity of the protein adsorbed onto the surface. The results are shown in FIGS. 4 and 5, respectively.

Figure 4:
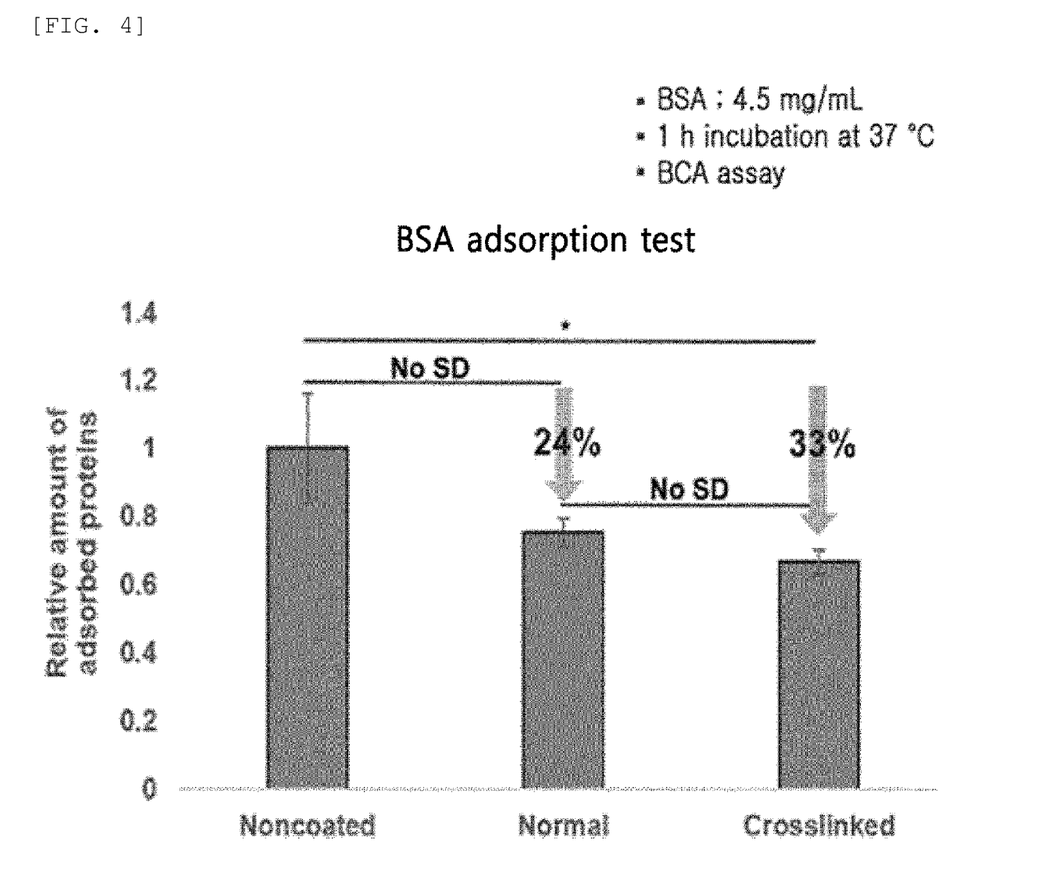
FIG. 4 shows a reduction rate of BSA adsorption on the surface prepared by the coating method using crosslinking according to the present invention or the surface prepared by the normal coating method with, respect to BSA adsorption, on the non-coated surface.
Figure 5:
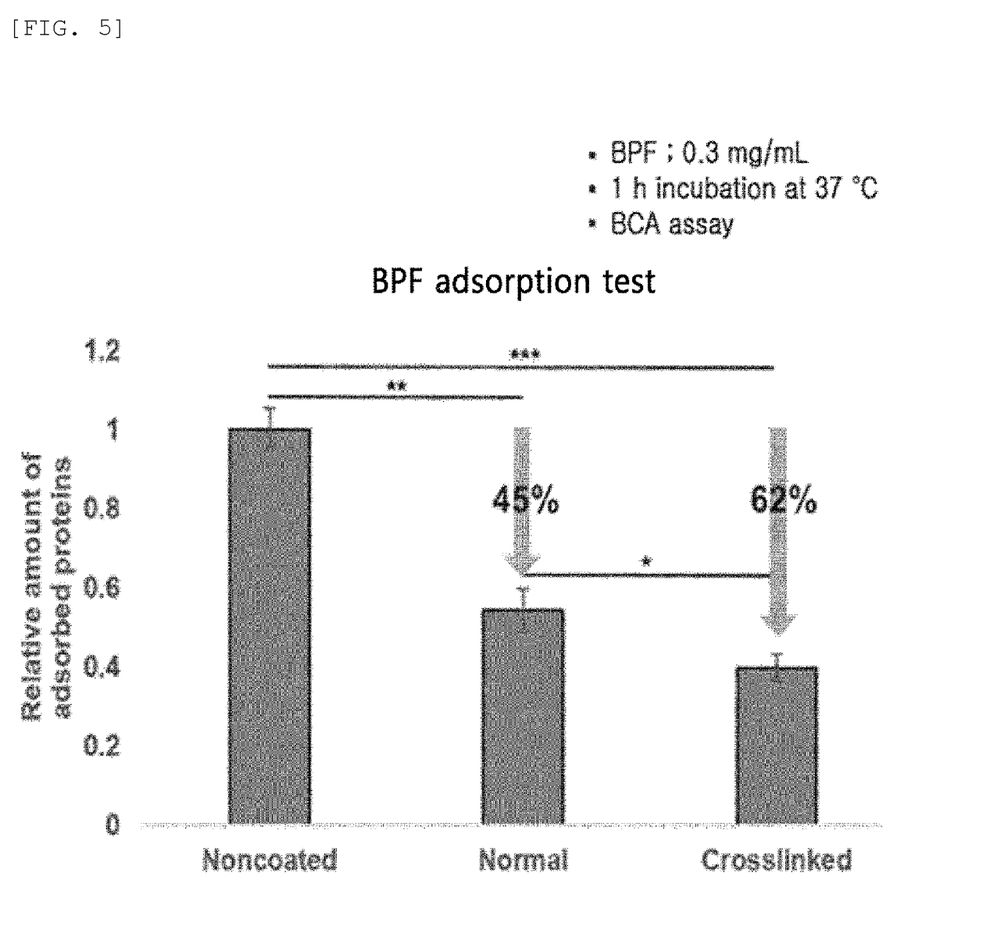
FIG. 5 shows a reduction rate of EPF adsorption on the surface prepared by the coating method using crosslinking according to the present invention or the surface prepared by the normal coating method with respect to BPF adsorption on the non-coated surface.

As shown in FIGS. 4 and 5, compared to the non-coated surface, the PMPC-coated surface and the crosslinked PMPC-coated surface showed 24% reduction and 33% reduction in BSA adsorption onto the PDMS surface, respectively. Compared, to the non-coated surface, the PMPC-coated surface and the crosslinked PMPC-coated surface showed 45% reduction and 62% reduction in BPF adsorption onto the PDMS surface, respectively. That is, both BSA and BPF adsorptions were reduced in the PMPC-coated surface, compared to the non-coated surface, and in particular, more remarkably reduced protein adsorption was observed in the crosslinked PMPC-coated surface.

Experimental Example 4: Measurement of Cell Adsorption

Based on the fact that capsular contracture is closely related to excessive proliferation of fibroblasts and collagen production thereby, fibroblast NIH 3T3 cells were cultured on PDMS which was coated with crosslinked or non-crosslinked PMPC prepared in Example 1 (Crosslinked) and Comparative Example 1 (Normal), and ceil adsorption was examined. The NIH-3T3 cells were cultured in a DMEM medium containing 10% FBS at 5% carbon dioxide and 37° C., 30,000 ceils per PDMS with a diameter of 1.5 cm were dispensed, and cultured at 5% carbon dioxide and 37° C. for 45 hours, and then washed lightly with fresh DMEM medium (containing 10% FBS), followed, by CCK assay. A CCK solution of Dojindo Co. Ltd. was used, and each of the washed PDMS was immersed in a fresh DMEM medium (containing 10% FBS), and the CCK solution was added at a volume corresponding to 10% of the medium volume, followed by incubation at 5% carbon dioxide and 37° C. for 4 hours. Absorbance at 450 nm was measured to determine the relative quantity of the cells adsorbed onto the surface. The results are shown in FIG. 6.

Figure 6:
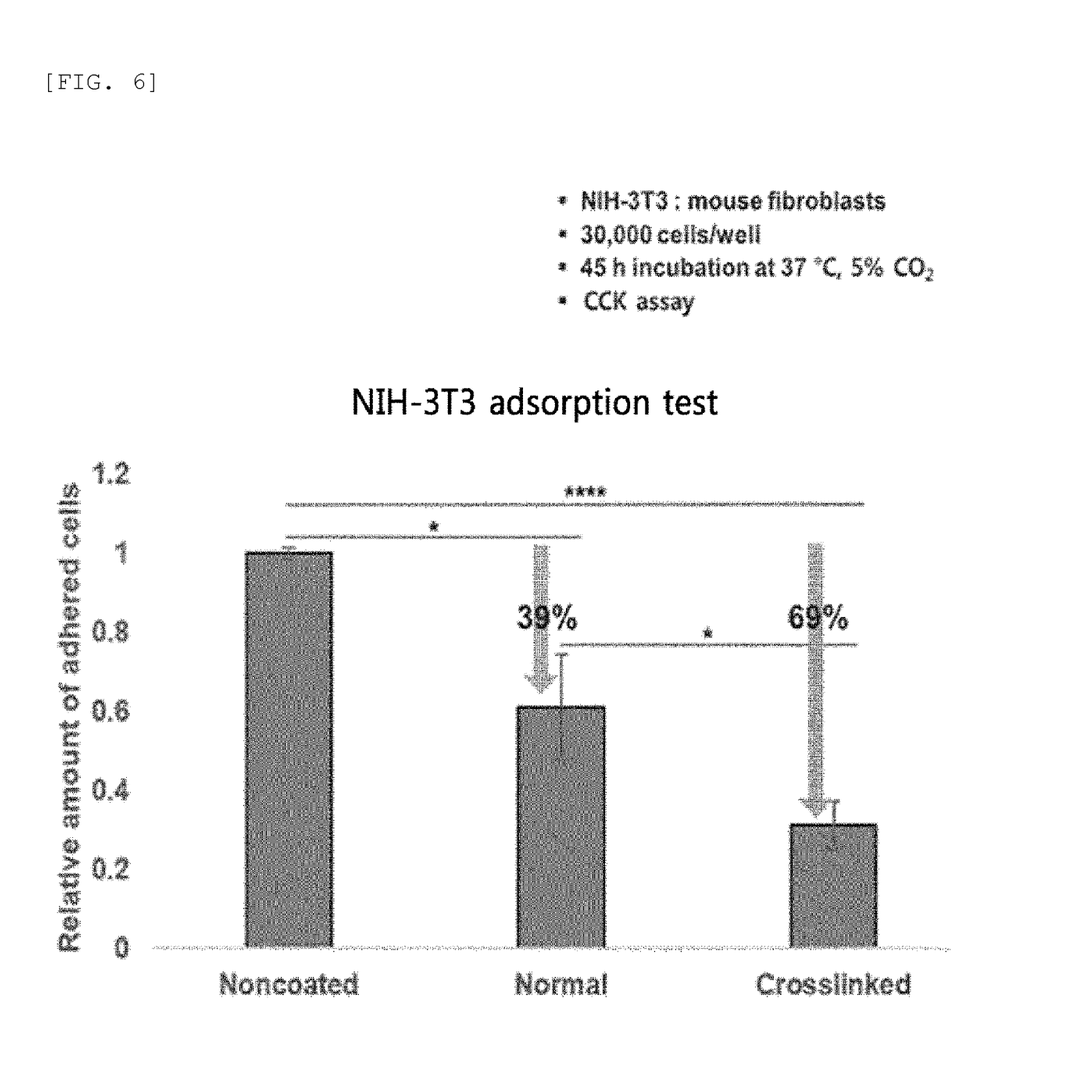
FIG. 6 shows a reduction rate of cell (NIH-3T3) adsorption on the surface prepared by the coating method using crosslinking according to the present invention or the surface prepared by the normal coating method with respect to cell (NIH-3T3) adsorption on the non-coated surface.

As shown in FIG. 6, a remarkable reduction (39% reduction) in surface adsorption of fibroblasts was observed in the PMPC-coated surface, compared to the non-coated. PDMS. Further, a more remarkable reduction (69% reduction) in surface adsorption of fibroblasts was observed in the crosslinked PMPC-coated surface. Therefore, side effects such as capsular contracture due to excessive proliferation of fibroblasts after surgery may be remarkably reduced, and as shown in Example 1, PDMS coated with crosslinked PMPC according to the present invention maintained the coating condition even under strong mechanical stimulation. Therefore, it is expected, that the coating may be maintained upon vigorous activity or over time after cosmetic surgery, thereby reducing side effects due to peeling of the coating.

Experimental Example 5: Measurement of In Vivo Capsule Formation

Figure 7:
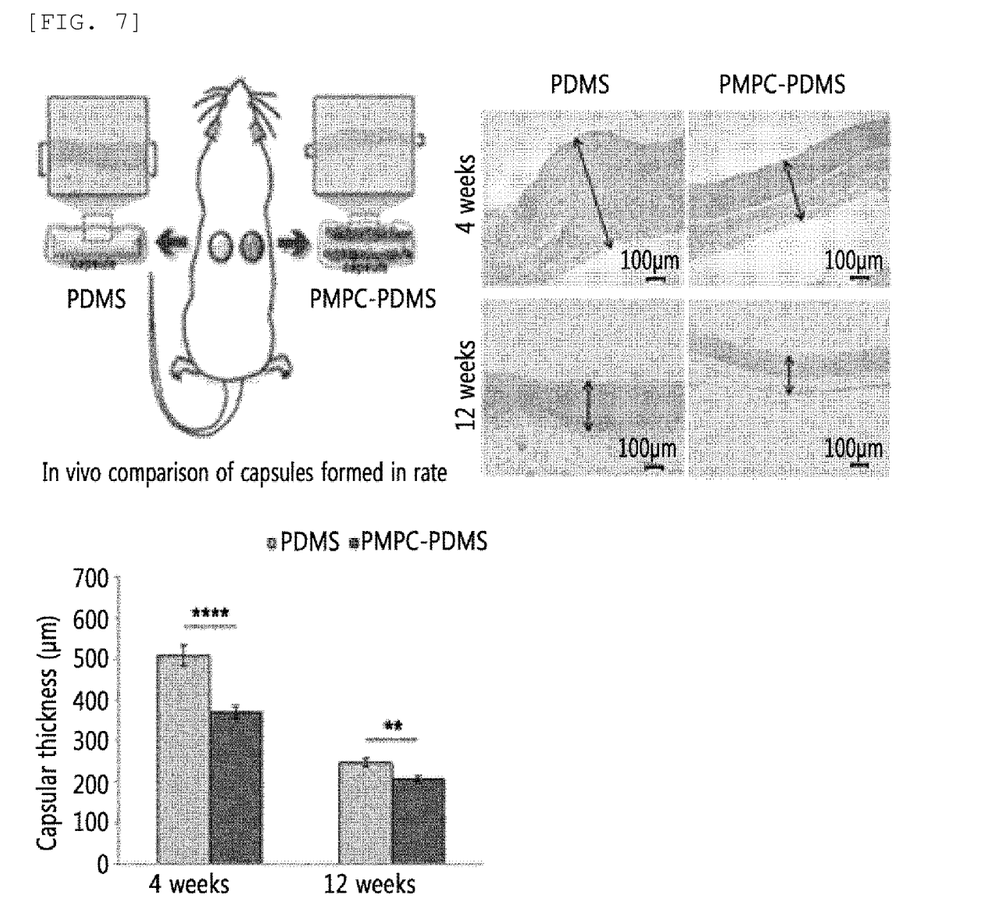
FIG. 7 shows the thickness of capsule formed on a prosthesis implanted to a rat, which was observed under a microscope after H&E staining.

A PDMS block surface-coated with PMPC and a non-surface treated PDMS block as a control group were implanted to the left and right of the back of a Sprague-Dawley rat, respectively. The rat was raised for 1 month and 3 months, and then reactions in the body were observed. First, the thickness of the capsule formed, surrounding the surface of the implant was measured. After H&E staining, the thickness of the capsule was observed under a microscope, and the results are shown in FIG. 7. As shown in FIG. 7, the thickness of the capsule formed on the surface of the PMPC-coated EDMS block implanted in the body was thinner than that of the capsule formed, on the control group, at both 1 month and 3 months. Such a reduction in the capsule formation on the PMPC-coated implant indicates a reduction of foreign body reaction, by the coating. Furthermore, cellularity and vascularity were measured and shown in FIG. 8, and TGF-β, α-SMA (smooth muscle actin), myeloperoxidase, and CD34 expression levels were measured by immunohistochemistry and shown in FIG. 9.

Figure 8:
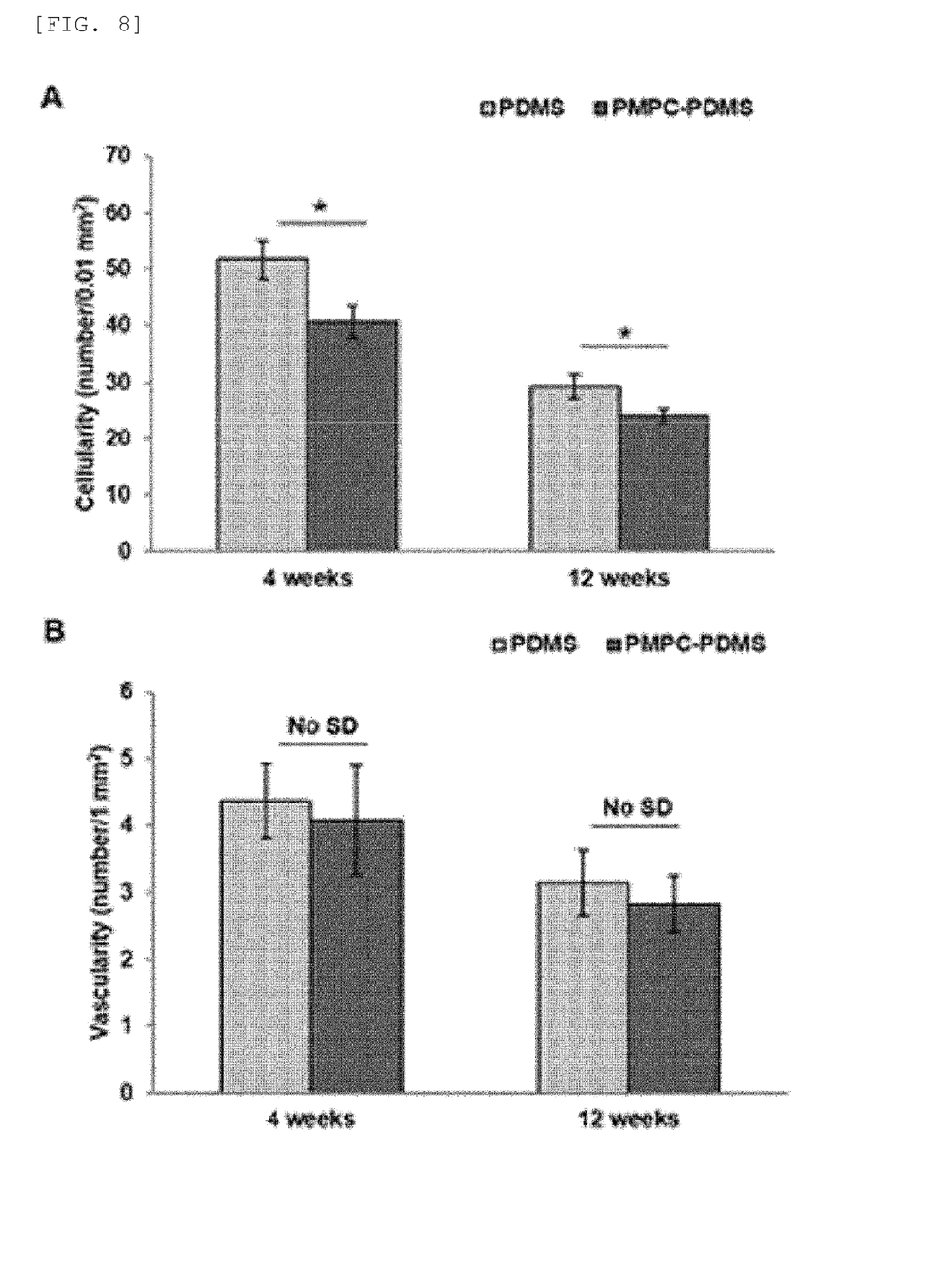
FIG. 8 shows the result of measuring cellularity and vascularity at 4 weeks and 12 weeks after implantation of a prosthesis to rats.
Figure 9:
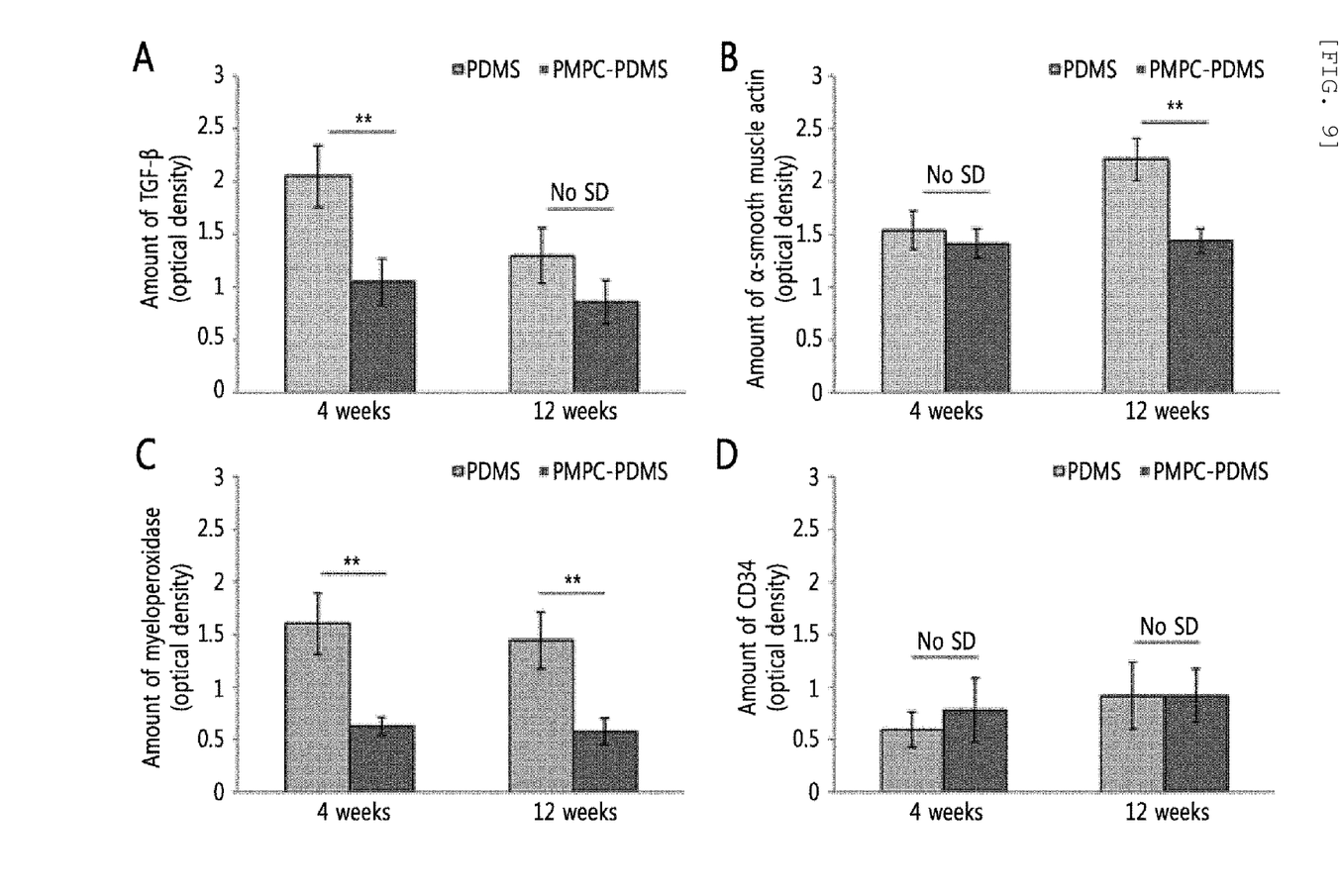
FIG. 9 shows TGF-$\beta$, $\alpha$-SMA (smooth muscle actin), myeloperoxidase, and CD34 expression levels which were measured in prosthesis-implanted rats by immunohistochemistry.

As a result, when the PMPC-coated. PDMS was implanted, the number of inflammatory cells was remarkably reduced, and an inflammatory index, myeloperoxidase level was also remarkably reduced at both 1 month and 3 months, compared to the control group. Further, an index of inflammation and fibrous tissue formation, TGF-β or α-SMA was also remarkably reduced at 1 month and 3 months, compared to the control group. These results correspond to the order of the reduction in fibrous tissue formation following the reduction of the tissue inflammation in the time sequence of capsule formation. In contrast, there was no significant difference in the expression of an angiogenic marker CD34, indicating that there is little relationship between foreign body reaction and angiogenesis.

Effect of the Invention

An in-vivo implantable prosthesis coated with crosslinked polyphosphorylcholine may be manufactured by a simple method of applying a coating composition including a photoinitiator, a crosslinking agent, and a phosphorylcholine (PC) monomer having an acrylate group according to the present invention, and then irradiating UV rays. The crosslinked polyphosphorylcholine coating may provide hydrophilicity for the surface and may also remarkably reduce adsorption of proteins and fibroblasts, which may cause side effects such as capsular contracture. Further, the coating has strong enough not to peel off even under mechanical stimulation, and therefore, it is maintained under vigorous activity after implantation, thereby being usefully applied to the manufacture of an in-vivo implantable prosthesis with reduced side effects, such as breast prosthesis for cosmetic surgery.

What is claimed is:

1. A method of coating an in-vivo implantable prosthesis, comprising:
    applying a coating composition comprising a photoinitiator, a crosslinking agent, and a phosphorylcholine monomer having an acrylate group to an external surface of the in-vivo implantable prosthesis; and
    irradiating UV rays onto the in-vivo implantable prosthesis to which the coating composition is applied, thereby forming crosslinked polyphosphorylcholine which is covalently bonded with the external surface of the in-vivo implantable prosthesis,
    wherein the external surface material of the in-vivo implantable prosthesis includes polydimethylsiloxane.

2. The method of claim 1, wherein the phosphorylcholine monomer having the acrylate group is methacryloyloxyethylphosphorylcholine or acryloyloxyethylphosphorylcholine.

3. The method of claim 1, wherein the photoinitiator is selected from the group consisting of benzophenone, benzoyl peroxide, azobisisobutyronitrile, and 2,2-dimethoxy-2-phenylacetophenone.

4. The method of claim 1, wherein the crosslinking agent is selected from the group consisting of dipentaerythritol pentaacrylate, dipentaerythritol hexaacrylate, ethyleneglycol diacrylate, ethyleneglycol dimethacrylate, allyl methacrylate, acetoacetoxyethyl methacrylate, isocyanatoethyl methacrylate, and combinations thereof.

5. The method of claim 1, comprising the photoinitiator in an amount of 0.01 to 0.2 mol % with respect to the phosphorylcholine monomer.

6. The method of claim 1, comprising the crosslinking agent in an amount of 0.01 to 2.0 mol % with respect to the phosphorylcholine monomer.

7. The method of claim 1, wherein the coated prosthesis inhibits capsular contracture or foreign body reaction around the in-vivo implantable prosthesis when implanted as compared to an uncoated in-vivo implantable prosthesis.

8. The method of claim 1, wherein the external surface material of the in-vivo implantable prosthesis comprises polydimethylsiloxane having a functional group which provides a radical that binds to a terminal C=C bond of the acrylate group via the photoinitiator.

* * * * *